(12) United States Patent
Liu et al.

(10) Patent No.: US 8,086,410 B1
(45) Date of Patent: Dec. 27, 2011

(54) METHODS OF DETECTING DNA VARIATION IN SEQUENCE DATA

(76) Inventors: Changsheng Liu, State College, PA (US); Fei Gao, State College, PA (US)

( * ) Notice: Subject to any disclaimer, the term of this patent is extended or adjusted under 35 U.S.C. 154(b) by 561 days.

(21) Appl. No.: 12/117,911

(22) Filed: May 9, 2008

Related U.S. Application Data

(62) Division of application No. 10/447,338, filed on May 29, 2003, now Pat. No. 7,400,980.

(51) Int. Cl.
*G06F 19/00* (2011.01)
*C12Q 1/68* (2006.01)

(52) U.S. Cl. .................. 702/19; 702/20; 435/6

(58) Field of Classification Search .......... None
See application file for complete search history.

(56) References Cited

U.S. PATENT DOCUMENTS

2002/0147548 A1* 10/2002 Walther et al. .................. 702/20

OTHER PUBLICATIONS

Bonfield et al. (Nucleic Acids Research (1998) vol. 26, pp. 3404-3409).*
Mattocks et al. (Human Mutation (2000) vol. 16, pp. 437-443).*
Staden et al. (Bioinformatics: A Practical Guide to the Analysis of Genes and Proteins, Second Edition (2001) Baxevanis and Ouellette, Eds., John Wiley & Sons, Inc.).*

* cited by examiner

*Primary Examiner* — Lori A Clow
(74) *Attorney, Agent, or Firm* — John J. Elnitski, Jr.

(57) ABSTRACT

A method for detecting DNA variation. First, by aligning trace data of a sample DNA sequence to trace data of a reference DNA sequence to produce an aligned sample DNA sequence. Then, inputting the trace data of the bases of both the reference DNA sequence and the aligned sample DNA sequence for a particular frame number into a non-linear mathematical function of an anti-correlation calculation scheme for all the frame numbers. Minimal values will be produced at the particular frame number for DNA base trace data of the aligned sample DNA sequence which are not a variation as compared to the reference DNA sequence. Values above the minimal values will be produced at the particular frame number for DNA base trace data of the aligned sample DNA sequence which are a variation as compared to the reference DNA sequence.

12 Claims, 11 Drawing Sheets

SEQUENCE LISTING

<160> NUMBER OF SEQ ID NOS: 23

<210> SEQ ID NO 1
<211> LENGTH: 14
<212> TYPE: DNA
<213> ORGANISM: Unknown
<220> FEATURE:
<223> OTHER INFORMATION: It is an example listing

<400> SEQUENCE: 1
aatttttctt tggg                                                             14

<210> SEQ ID NO 2
<211> LENGTH: 12
<212> TYPE: DNA
<213> ORGANISM: Unknown
<220> FEATURE:
<223> OTHER INFORMATION: It is an example listing

<400> SEQUENCE: 2
aatttttttg gg                                                               12

<210> SEQ ID NO 3
<211> LENGTH: 10
<212> TYPE: DNA
<213> ORGANISM: Unknown
<220> FEATURE:
<223> OTHER INFORMATION: It is an example listing

<400> SEQUENCE: 3
tgatgtttga                                                                  10

<210> SEQ ID NO 4
<211> LENGTH: 39
<212> TYPE: DNA
<213> ORGANISM: Homo sapiens

<400> SEQUENCE: 4
cagaatgtag gacagagggc atgctcggta aatatgtgt                                  39

<210> SEQ ID NO 5
<211> LENGTH: 38
<212> TYPE: DNA
<213> ORGANISM: Homo sapiens
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 5
cgnntgtagg acagagggca tgctnggtaa atatgtgt                                   38

<210> SEQ ID NO 6
<211> LENGTH: 38
<212> TYPE: DNA
<213> ORGANISM: Homo sapiens
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (25)..(25)

<223> OTHER INFORMATION: n is a, c, g, or t

<400> SEQUENCE: 6
cgnntgtagg acagagggca tgctnggtaa atatgtgt                          38

<210> SEQ ID NO 7
<211> LENGTH: 30
<212> TYPE: DNA
<213> ORGANISM: Homo sapiens

<400> SEQUENCE: 7
gttatttcct tatttcctta gatccaaatc                                   30

<210> SEQ ID NO 8
<211> LENGTH: 29
<212> TYPE: DNA
<213> ORGANISM: Homo sapiens

<400> SEQUENCE: 8
gttatttcct tctttgttag atccaaatc                                    29

<210> SEQ ID NO 9
<211> LENGTH: 11
<212> TYPE: DNA
<213> ORGANISM: Homo sapiens

<400> SEQUENCE: 9
accggagatc t                                                       11

<210> SEQ ID NO 10
<211> LENGTH: 11
<212> TYPE: DNA
<213> ORGANISM: Homo sapiens

<400> SEQUENCE: 10
accgagatct t                                                       11

<210> SEQ ID NO 11
<211> LENGTH: 10
<212> TYPE: DNA
<213> ORGANISM: Homo sapiens

<400> SEQUENCE: 11
accgagatct                                                         10

<210> SEQ ID NO 12
<211> LENGTH: 11
<212> TYPE: DNA
<213> ORGANISM: Homo sapiens

<400> SEQUENCE: 12
accggagatc t                                                       11

<210> SEQ ID NO 13
<211> LENGTH: 11
<212> TYPE: DNA
<213> ORGANISM: Homo sapiens
<220> FEATURE:
<221> NAME/KEY: misc_feature
<222> LOCATION: (5)..(10)
<223> OTHER INFORMATION: n is a, c, g, or t

<400> SEQUENCE: 13
accgnnnnnn t                                                       11

```
<210> SEQ ID NO 14
<211> LENGTH: 11
<212> TYPE: DNA
<213> ORGANISM: Homo sapiens

<400> SEQUENCE: 14
accggagatc t                                                              11

<210> SEQ ID NO 15
<211> LENGTH: 11
<212> TYPE: DNA
<213> ORGANISM: Homo sapiens

<400> SEQUENCE: 15
accgagatct t                                                              11

<210> SEQ ID NO 16
<211> LENGTH: 10
<212> TYPE: DNA
<213> ORGANISM: Homo sapiens

<400> SEQUENCE: 16
accgagatct                                                                10

<210> SEQ ID NO 17
<211> LENGTH: 72
<212> TYPE: DNA
<213> ORGANISM: Homo sapiens

<400> SEQUENCE: 17
gtggcactgt tgtttcacaa gatgatgttt gaaactattc caatgttcag tggcggaact         60
tgcagtaagt gc                                                             72

<210> SEQ ID NO 18
<211> LENGTH: 45
<212> TYPE: DNA
<213> ORGANISM: Homo sapiens

<400> SEQUENCE: 18
gtggcactgt tgtttcacaa gaatttaatc ggttggaact gaaat                         45

<210> SEQ ID NO 19
<211> LENGTH: 50
<212> TYPE: DNA
<213> ORGANISM: Homo sapiens

<400> SEQUENCE: 19
tgatgtttga aactattcca atgttcagtg gcggaacttg cagtaagtgc                    50

<210> SEQ ID NO 20
<211> LENGTH: 49
<212> TYPE: DNA
<213> ORGANISM: Homo sapiens

<400> SEQUENCE: 20
aactattcca atgttctggc ggaacttgca gtaagtgctt gaaattctc                     49

<210> SEQ ID NO 21
<211> LENGTH: 39
<212> TYPE: DNA
<213> ORGANISM: Homo sapiens

<400> SEQUENCE: 21
```

```
aactattcca atgttcatgg cggaacttgc agtaagtgc                    39

<210> SEQ ID NO 22
<211> LENGTH: 20
<212> TYPE: DNA
<213> ORGANISM: Homo sapiens

<400> SEQUENCE: 22
tctttcttac attccattta                                         20

<210> SEQ ID NO 23
<211> LENGTH: 20
<212> TYPE: DNA
<213> ORGANISM: Homo sapiens

<400> SEQUENCE: 23
tctttcttac attccattta                                         20
```

METHODS OF DETECTING DNA VARIATION IN SEQUENCE DATA

This application is a Divisional application of U.S. patent application Ser. No. 10/447,338, filed on May 29, 2003 and also claims the benefit of and hereby incorporates by reference U.S. Provisional Application No. 60/384,280 filed May 30, 2002.

BACKGROUND

The present invention generally relates to detection of DNA variations. More specifically, the present invention relates to methods for automatic detection of DNA mutations and polymorphisms using human sequencing trace data.

Mutation detection is increasingly undertaken as a tool for wide spectrum of research in disease diagnostics, especially in cancer research. Many pharmaceutical companies spend billions of dollars to locate the mutate genes associated with any one particular disease. There are many technologies available to detect a mutation indirectly. The following are examples of the many indirect methods available to detect DNA variation in a specific region of DNA from multiple samples. One such series of indirect methods is referred to as mutation discovery methods. Mutation discovery methods detect the relative peak shifting when a mutation sample is compared to wild-type reference DNA. The mutation discovery methods include denaturing gradient gel electrophoresis (DGGE), denaturing high performance liquid chromatography (DHPLC), temperature gradient capillary electrophoresis (TGCE), heteroduplex analysis (HD), the analysis of single stranded DNA conformation polymorphism (SSCP), and chemical or enzyme cleavage of the mismatch (CECM). The mutation discovery methods are "blind" without knowing the specific location of DNA sequencing. Therefore, the mutation discovery methods cannot tell where the mutation has taken place and what type of mutation is in a DNA sample. All of these mutation discovery methods are indirect and requires confirmation of mutations by DNA sequencing. Another series of indirect methods is referred to as mutation genotyping. An example of mutation genotyping is the single base extension method, which detects mutation type when the DNA sequence is known. The above two series of indirect methods involve comparing two peaks in the electropherogram.

A more direct series of methods are referred to as DNA sequencing, which detects the mutation location and mutation type in the sample and provides accurate mutation information. However, DNA sequencing involves a large amount of calculation and extensive data manipulation to find the mutations. The mutation detection from DNA sequence data is cumbersome and time consuming and is currently based on visual inspection. The visual inspection is required because base-calling error percentage (1~1.5%) is much higher than mutation percentage (0.05~0.2%). A software program using computer hardware for automatic detection of mutation from sequence trace data appears to be the most prudent method to hunt for mutations in disease and cancer genes. There are academic software programs for mutation detection using trace data. However, the academic software programs can detect only a specific type of mutation with a specific chemistry. None of them are capable of detecting all kinds of mutations with all chemistries. Other drawbacks to the available academic software programs are errors, lack of flexibility, requirement of visual inspection of final results due to errors and cumbersome of use. Also, comparison methods have been discussed in a few scientific papers to find heterozygous mutation from DNA sequence traces with a linear trace subtraction method. But, there is no known paper discussing detection of insertion and deletion mutations, especially heterozygous insertions and deletions.

It is an object of the present invention to provide a method which can be implemented with software for the automatic detection of DNA mutation from sequence trace data.

It is another object of the present invention to provide a method with can be used for the detection of insertion and deletion DNA mutations from sequence trace data.

SUMMARY OF THE INVENTION

A method for detecting DNA variation. First, by aligning trace data of a sample DNA sequence to trace data of a reference DNA sequence to produce an aligned sample DNA sequence. Then, inputting the trace data of the bases of both the reference DNA sequence and the aligned sample DNA sequence for a particular frame number into a non-linear mathematical function of an anti-correlation calculation scheme for all the frame numbers. Minimal values will be produced at the particular frame number for DNA base trace data of the aligned sample DNA sequence which are not a variation as compared to the reference DNA sequence. Values above the minimal values will be produced at the particular frame number for DNA base trace data of the aligned sample DNA sequence which are a variation as compared to the reference DNA sequence.

DETAILED DESCRIPTION

Figure 1:
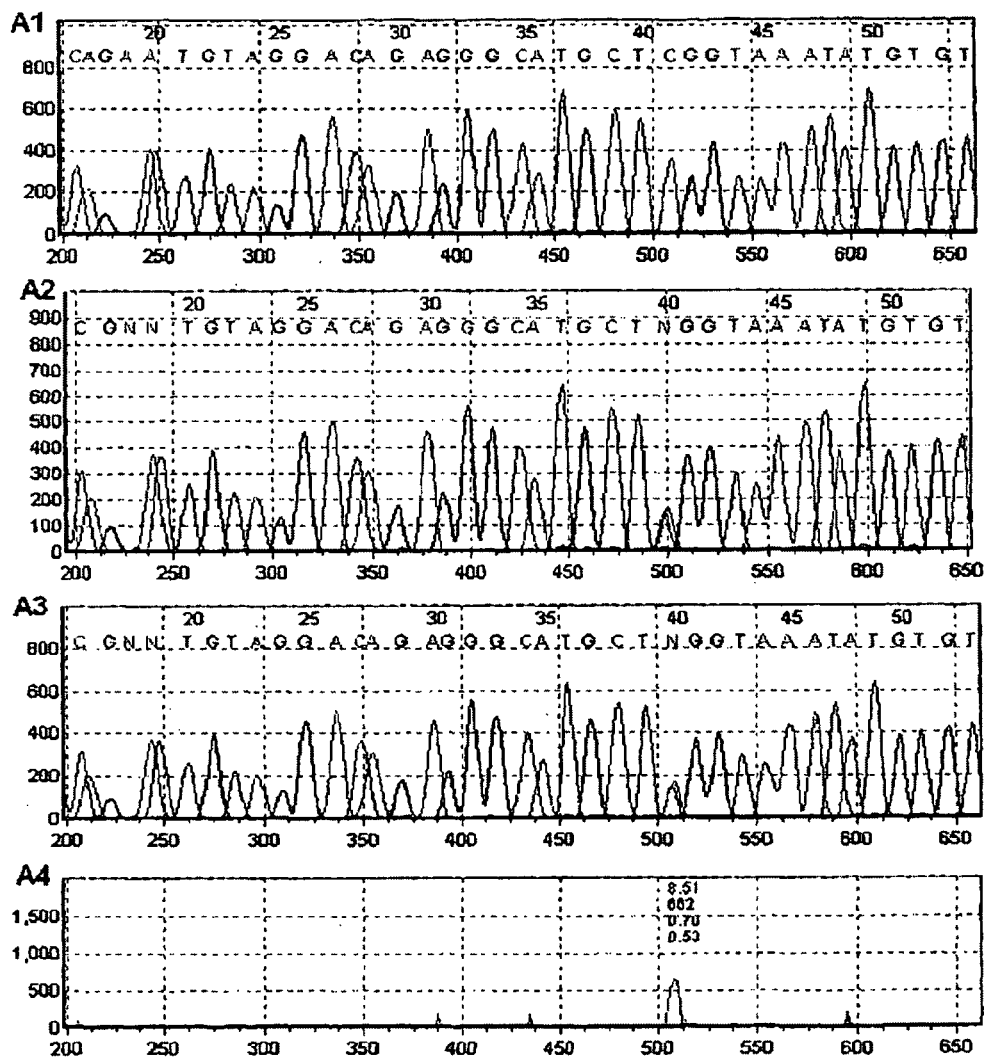
FIG. 1 is a series of electropherograms to depict a DNA variation according to the present invention. (seq. ID No. 4-6)

The present invention is a method of detecting DNA variations in sequence data by automatic detection. The method detects all kinds of mutations including homozygotes, heterozygotes, insertions and deletions, and heterozygous insertion and deletion. The mutation detection is based on comparison between the mutant sample sequence and a wild-type reference sequence. Currently, the percentage of basecalling error is about 1~1.5%, and percentage of mutation in mutant samples is about 0.05~0.2%. The discovery of a mutation can be hidden in a high background of noise due to base-calling errors. The method uses the trace data of a sequence, thereby making the mutation detection immune to basecalling errors from analytical software.

Sequence trace data is usually taken from an automatic fluorescence DNA sequencer instrument, such as a slab gel or capillary type instrument. Examples of such instruments are the Aplied Biosystem 3730, 377, 3100 genetic analyzers, or Molecular Dynamics magaBace DNA analysis system. The data from the sequencer instrument provides four traces of data plotted in an electropherogram. The four traces of data correspond to G, A, T, and C bases in a sequence, as shown by plots A1, A2 in FIG. 1. Whereby, plot A1 is a plot of a reference sequence trace data and plot A2 is a plot of a sample sequence trace data. The four traces of data plotted are usually shown in a different color for each of the four bases, creating four different colored lines of data. The method aligns the sequence trace data of the sample and the reference. The method employs computer software using anti-correlation techniques to identify the mutations from DNA sequence data. The method detects both the location of the mutation and the type of mutation from the sequence trace. The method is sensitive to the difference between the trace data of the reference and the sample. The method is used to find any insertion or deletion in the sample sequence. The method employs a two direction mutation calculation to confirm results. The method also includes a mutation score using the multiple available mutation parameters to provide a confidence level of the mutation peaks. The mutation score calculations are based on the types of mutation, which are homozygotes, heterozygotes, insertion and deletion.

The anti-correlation technique automatically detects the difference between the mutant sample and wide-type reference sequences, after both sequences are aligned. At a specific frame number, if both sample and reference are of the same type of base trace, such as A base, the anti-correlation value will be zero. If both sequences show different base traces, such as G and T bases, then the anti-correlation will have a very high value dependent on the trace data intensities. The signal noise in the trace data inherent from the sequencer instrument will not affect the mutation result, because anti-correlation picks up the high intensity more quickly than lower intensity values. Since this is a correlation technique, the method does not need to align the peaks perfectly. With the trace data, the mutation call of the method is sensitive to the real physically-happening mutations, but not sensitive to basecall errors.

Figure 2:
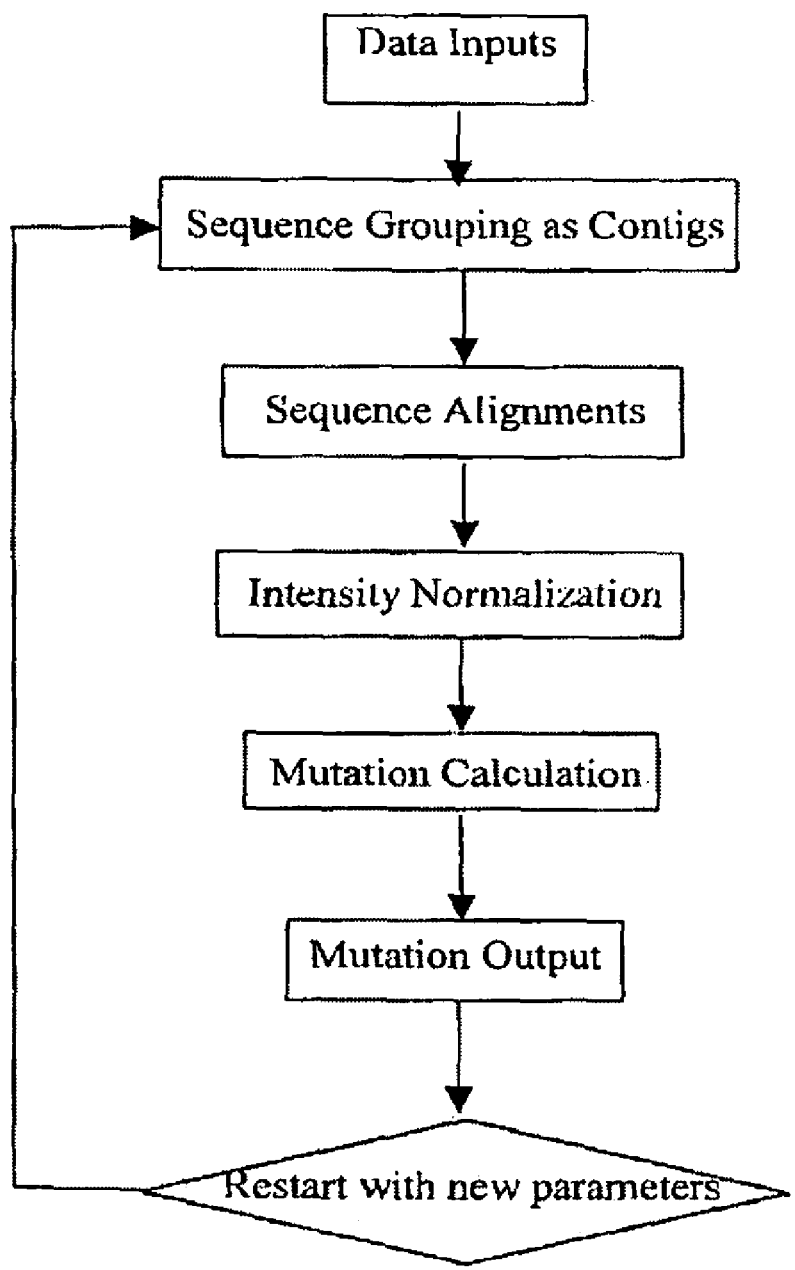
FIG. 2 is a flow diagram the method according to the present invention.

FIG. 2 shows a flow chart of the method of the present invention to be implemented into computer software for detecting DNA variations. The first step in FIG. 2 is to provide input of trace data and sequence letter data. The trace data inputs which also includes sequence letter data are from reference DNA data files and sample DNA data files. Additional sequence letter data used as a reference guide is from GENBANK DNA data files which only contain sequence letters and is associated with the GENBANK database. The reference DNA data files selected do not contain any signs of mutation or disease, or are from control DNA. The sample DNA data files are of the sequence to be tested. There are usually two types of files associated with the inputted data. The first type are *.scf or *.abl files which contain DNA trace data and sequence letters information and are associated with both reference DNA data files and sample DNA data files. The second type are *.seq or *.txt files which contain only sequence letters and are associated with the GENBANK DNA data.

The second step in FIG. 2 is the sequence grouping of the inputted trace data to determine if there are any Contigs. In this step, the reference sequence data is compared to sample sequence data to determine if there are any matches of sequence data between the reference and sample data. If two or more sequences are matched, there is a Contig. To determine if a Contig is present, there are two matching parameters in controlling the matching process. The two matching parameters are fragment size and fragment number. The two parameters can be adjusted by the user based on the user's requirements. The typical default values are twelve (12) for fragment size and five (5) for fragment number. These default values for fragment and fragment number indicate that if at least 5 fragments having 12 bases match, the two sequences are in the same Contig. Prior to Contig calculation, the reference files and GenBank data files are compared to find out if they match. If they match, more creditability is give to use of the reference file.

The third step of FIG. 2 is sequence alignment. Global alignment is a preliminary form of alignment of the sample and reference sequences. Global alignment is not the most accurate method of alignment, but is a general alignment of the sequences which is useful in getting a general picture of the trace data. Global alignment techniques are used to find the identical bases contained in the reference and sample sequences, then the sample trace data can be expanded or shrunk and shifted to match it to the reference trace data. In global alignment, the DNA bases are aligned to some degree. The peak centers of the same base in two sequences sometimes are frequently off by a couple of frame numbers, which will affect the mutation identification results. Sometimes, global alignment can create false positives, when dealing with overlapping peaks. There are means available to provide a more accurate alignment and align the peak centers of all of the matched bases, after global alignment has been performed. The following is an example of a way to obtain an accurate alignment after global alignment has been performed. First, attempt to find a region in the sequence with at least six bases that are identical in both the reference and sample trace data. Then, choose each peak maximum or peak weight center of the sample and force the bases of the sample to align with the peak maximum or peak weight center of the reference. The middle point between the peaks should be adjusted with a linear interpolation. If the bases of the sample and reference are different, then find the base difference and find two more bases, the one before and one after, making a total of three bases. Do not align with these three bases, but use the peaks, from the two sides of the three mutation bases to make alignment. The data points of the three bases are calculated using linear interpolation. If there are multiple peaks available, such as AATTTTTCTTTGGG (seq. ID No. 1), and AATTTTTTTGGG (seq. ID No. 2), the user may have difficulty identifying which T is the correct one to match for the alignment. In this case, start at GGG as reference point, then count peaks in the middle to find which peaks are matched peaks. For instance in the above example, the alignment would start at the third T from the left of the three G's. Finally after performing one of the above, calculate the new frame number and record the old and new frame numbers for later use. For example, an old frame number is 3457 for the sample sequence, then the calculated frame number is changed to a new frame number of 3342.6 for the sample trace date after global alignment to the reference traces. The new frame number is again changed to a newer number of 3342.9 after accurate alignment. The old frame number before global alignment and the new frame number after accurate alignment will be used later for the detection of insertion and deletion mutations. After accurate alignment has been performed, false positives should be significantly reduced. It has been found that the anti-correlation calculation method can tolerate the error of peak alignment and can also tolerate large alignment imperfection. However, the better the alignment, the better the mutation results. Plot A3 of FIG. 1 shows a plot of an alignment of the trace data from plots A1 and A2 of FIG. 1.

The fourth step of FIG. 2 is intensity normalization, which is the normalization of trace data values. Normalization is a known process to simplify the manipulation of values by normalizing the values, when there is a wide range of values due to different variables inherent in the process of creating data. The peak intensities values of all the bases can varied in a wide range, especially for chemistry of the dye-labeled terminator, where the dye molecule is attached to the end of DNA molecule. The intensity variation lies in two folds. One is that the different bases even in a local region show different intensities. The other variation is relative to the DNA size. The smaller DNA fragments, such as 100 base pairs, tend to have more intensity that of the large fragments, for example 700 bases. In contrast, the peak intensities are relatively uniform for the chemistry of the dye-labeled primer, where the dye attaches to the head of the DNA molecule. It is often the case to divide a whole trace into multiple sections with a fixed number of data points. For example, divide a trace into 30 sections and 300 data points per section. The median intensity of all of the peaks in the section is normalized to 3000 counts. The intensities of data points other than the median intensity are linearly extrapolated between two sections.

The fifth step of FIG. 2 is mutation calculation. The mutation calculation employs an anti-correlation calculation scheme using a non-linear mathematical function. The trace data from the reference and the sample are inputted into the non-linear mathematical function. An example of a linear mathematical function is where a and c are constants, I is trace intensities for G, A, T, C bases, and Var is the plotted variation value. The i, j represent any of the A, C, G, T traces. The t represents the data frame number, which is a migration time. A linear function is frequently not enough to pull the information of the mutation peaks. The linear function generates a mutation in the mutation electropherogram associating multiple peaks, such as positive peak, negative peak, and neighboring peaks. The linear function often results in much of the noise in the mutation detection due to the nature of dye terminator chemistry of the PCR reaction. A nonlinear mathematical function generates higher accurate mutation results than a linear function. The non-linear mathematical function can be any number of nonlinear mathematical functions to use the intensity values of the reference and sample sequence data. This can include the product, division, power, log, exponential operation, trigonometry functions, integration, deviation, and any other type of nonlinear function combination of above linear mathematical function. One example of the nonlinear mathematical function is Where $c_1$, $c_2$ and $c_3$ are constants, and $I_x(j,t)$ is the variable for intensity from the trace data of reference or sample sequences. For any mutation calculation, there are four individual data traces shown in one electropherogram for one sequence, whereby each data trace represents either G, A, T, or C. The intensity $I_r(j,t)$ represents the intensity of reference trace at a time t, where j=1, 2, 3, 4 standing for the four bases G, A, T, C. The intensity $I_s(j,t)$ represents the intensity of sample trace at a time t, where j=1, 2, 3, 4 standing for the four bases G, A, T, C. The entered data in a nonlinear mathematical function will produce 12 plotted traces of data to be plotted in a mutation electropherogram, due to four bases inputted into the nonlinear equation in pairs of i and j of the nonlinear function. Plot A4 of FIG. 1 is an example of such a plot of 12 traces of data in a mutation electropherogram.

The non-linear function produces a minimum value at a frame number for two base traces of the same letter of the sample and reference sequence data. If the two base traces in sample and reference are different at a frame number, the non-linear function produces a very high value, as compared to minimum value produced when the bases are the same. These values from the anti-correlation calculation method are used to produce a visual presentation to the user. The visual presentation discussed is an electropherogram called a mutation electropherogram, but the method is not limited to this type of presentation. The mutation electropherogram basically shows values to denote different bases for aligned reference and sample data overlapping in time, as shown by plot A4 in FIG. 1. This method ignores the base calling errors and detects real physical mutations. The mutation electropherogram shows mutations at 40 bps and ignores other 2 Ns at 18-19 bps in plot A3 of FIG. 1. This method of anti-correlation calculation method calculates base overlappings in time at the frame numbers, thereby creating an overlapping factor. The overlapping factor is defined as the percentage that peaks of sample and reference overlap in time. The higher overlapping factor, the more reliable the mutation calculation results. Ideally, the physical mutation peak will have 100% overlapping factor. The overlapping factor is used to eliminate some of the overlapping peaks due to mobility shift failure. The mobility shift sometimes can cause two peaks in two traces having 10-20% overlap, and therefore showing as false positives. Experience shows that if there is a false positive due to mobility shift, the overlapping factor is usually very small, 0.0-0.2. Whereby, the overlapping factor for mutation peak of a mutation is often 0.5~1.0, or 50~100%. Therefore, the overlapping factor is used to eliminate false positives.

Figure 3:
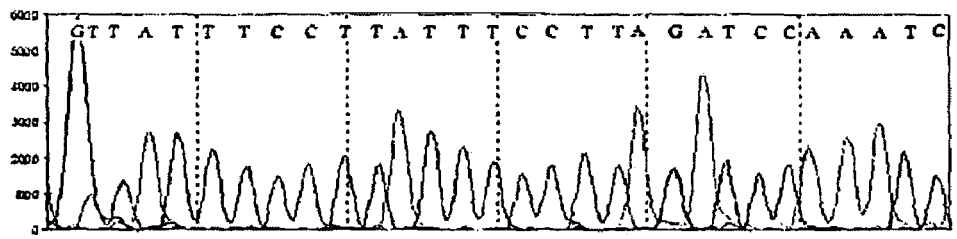
FIG. 3 is a reference DNA sequence electropherogram according to the present invention. (seq. ID No. 7)
Figure 4:
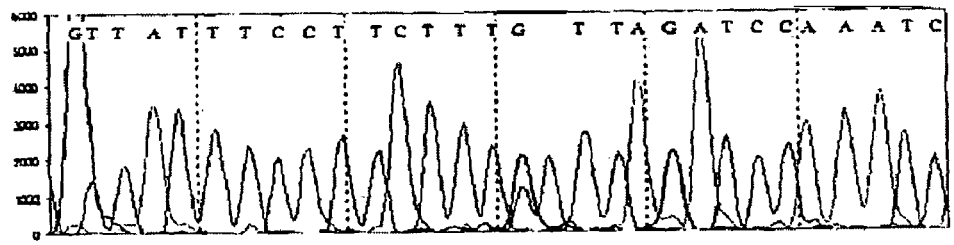
FIG. 4 is a sample DNA sequence electropherogram according to the present invention. (seq. ID No. 8)

It was determined that most nonlinear mathematical functions work fine for the mutation detections and the method of the present invention is not limited to the types of nonlinear mathematical functions disclosed. The following are examples of nonlinear mathematical functions and plots using the reference trace data of FIG. 3 and sample trace data of FIG. 4.

Figure 5:
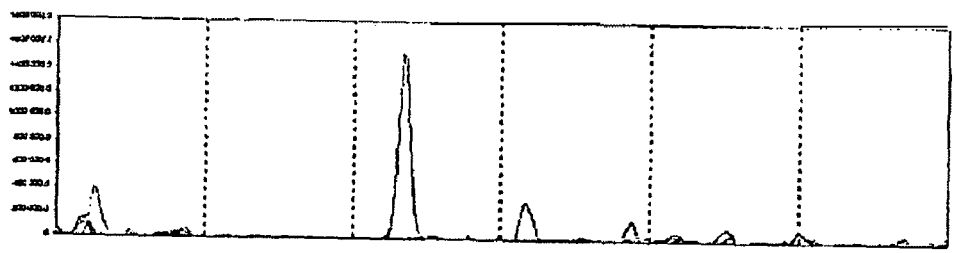
FIG. 5 is a mutation electropherogram according to the present invention.
Figure 6:
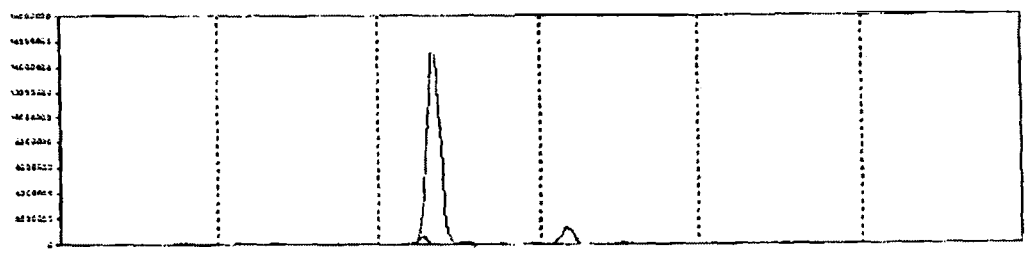
FIG. 6 is a mutation electropherogram according to the present invention.
Figure 7:
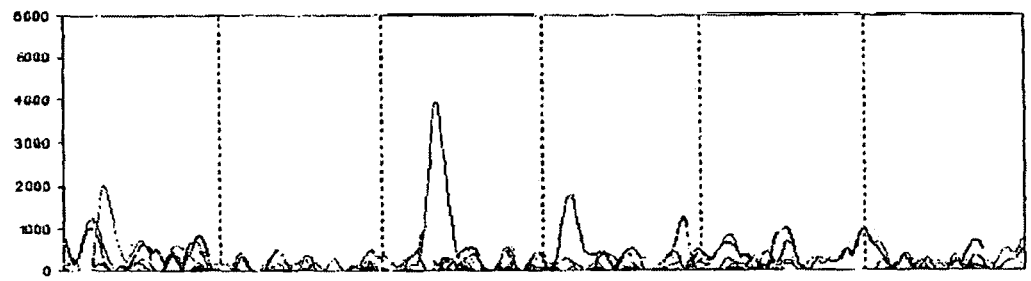
FIG. 7 is a mutation electropherogram according to the present invention.
Figure 8:
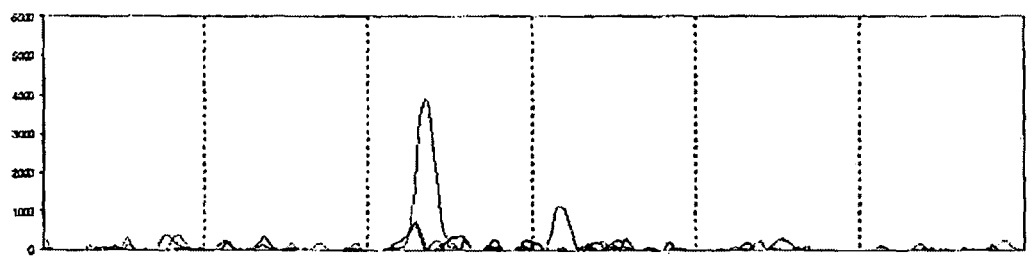
FIG. 8 is a mutation electropherogram according to the present invention.
Figure 9:
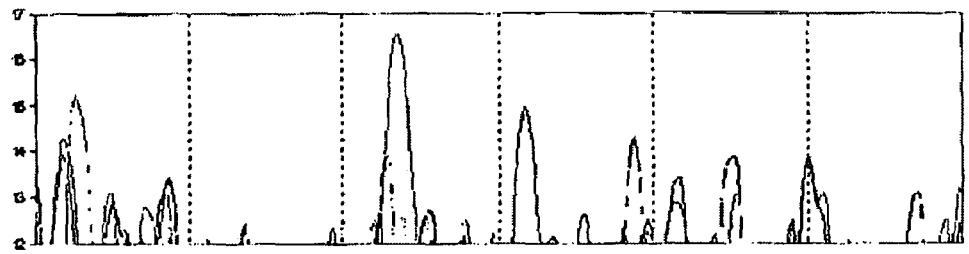
FIG. 9 is a mutation electropherogram according to the present invention.
Figure 10:
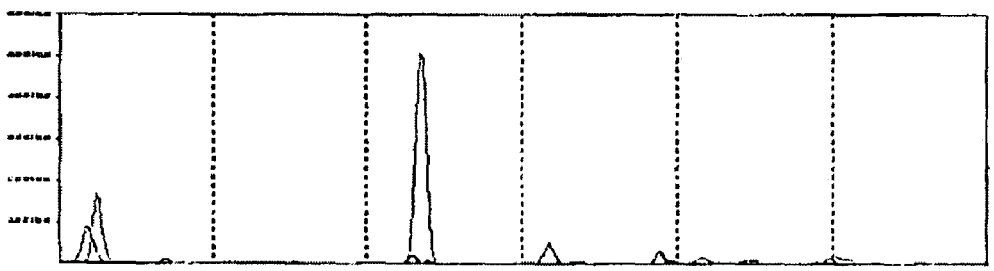
FIG. 10 is a mutation electropherogram according to the present invention.
Figure 11:
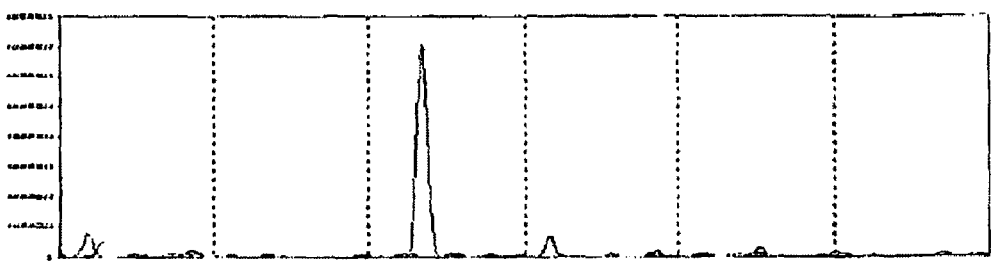
FIG. 11 is a mutation electropherogram according to the present invention.
Figure 12:
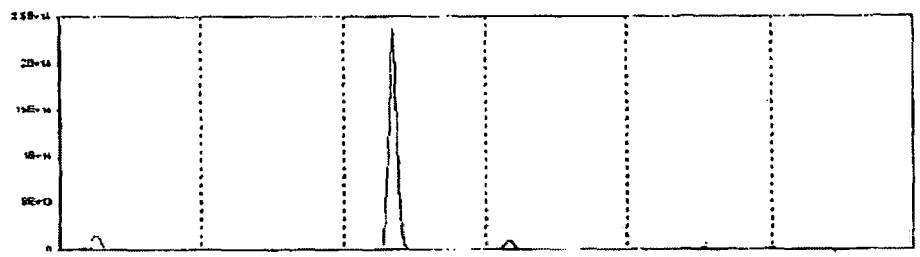
FIG. 12 is a mutation electropherogram according to the present invention.
Figure 13:
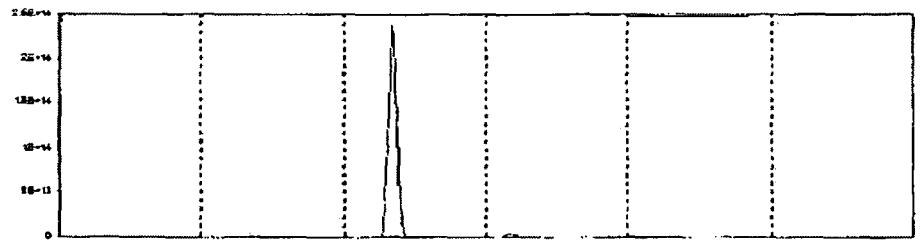
FIG. 13 is a mutation electropherogram according to the present invention.
Figure 14:
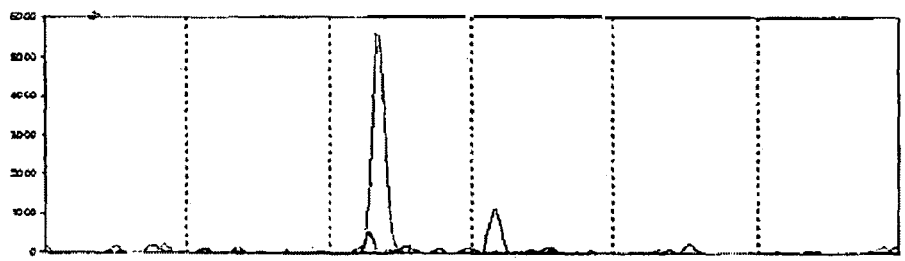
FIG. 14 is a mutation electropherogram according to the present invention.
Figure 15:
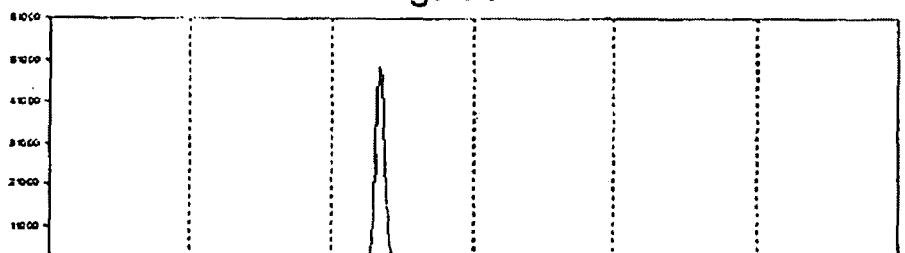
FIG. 15 is a mutation electropherogram according to the present invention.

Equation 1, results shown in FIG. 5
Equation 2, results shown in FIG. 6
  When $mu(i,j,t)>0$, using the top formula.
  $mu(i,j,t)=0$, when $mu(i,j,t)<0$ using the bottom formula;
Equation 3, results shown in FIG. 7
  when $mu(i,j,t)>0$;
  $mu(i,j,t))=0$ when $mu(i,j,t)<0$;
Equation 4, results shown in FIG. 8
  when $mu(i,j,t)>0$;
  $mu(i,j,t)=0$ when $mu(i,j,t)<0$;
Equation 5, results shown in FIG. 9
  when $I_r(i,t)>1$ and $I_s(j,t)>1$.
$mu(i,j,t)=0$ when $mu(i,j,t)<0$
Equation 6, results shown in FIG. 10
Equation 7, results shown in FIG. 11
Equation 8, results shown in FIG. 12
Equation 9, results shown in FIG. 13
When $mu>0$;
Other $mu=0$;
Equation 10, results shown in FIG. 14
when mu is real.
Equation 11, results shown in FIG. 15

The sixth step of FIG. 2 is mutation output. The mutation output is the output of data complied using the method. For the indication of mutations, 12 traces of data are plotted in the mutation electropherogram. FIGS. 5-15 and A4 of FIG. 1 all are mutation electropherograms which show peaks at mutation locations. When the method is implemented in software, the software detects peaks of mutation in the mutation electropherogram calculated with the above formulas.

Figure 16:
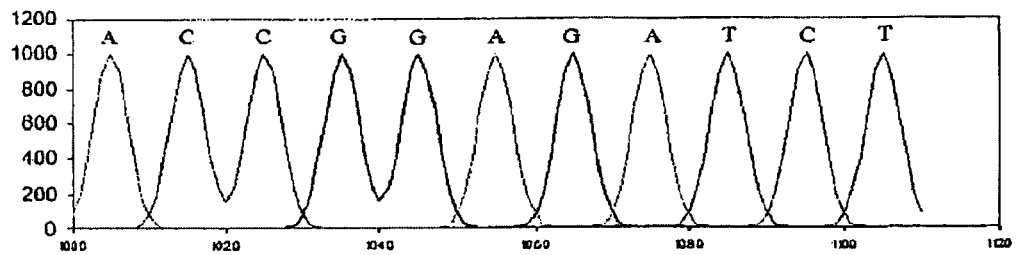
FIG. 16 is a reference DNA sequence electropherogram according to the present invention. (seq. ID No. 9)
Figure 17:
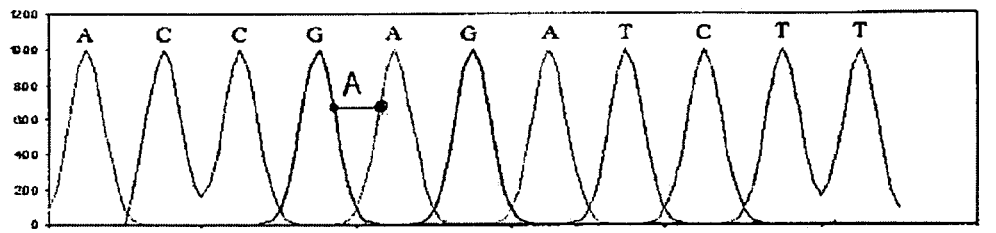
FIG. 17 is a sample DNA sequence electropherogram according to the present invention. (seq. ID No. 10)
Figure 18:
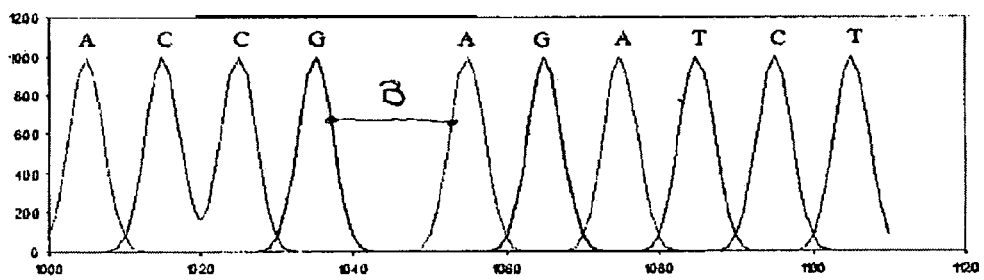
FIG. 18 is an aligned sample DNA sequence electropherogram according to the present invention. (seq. ID No. 11)
Figure 19:
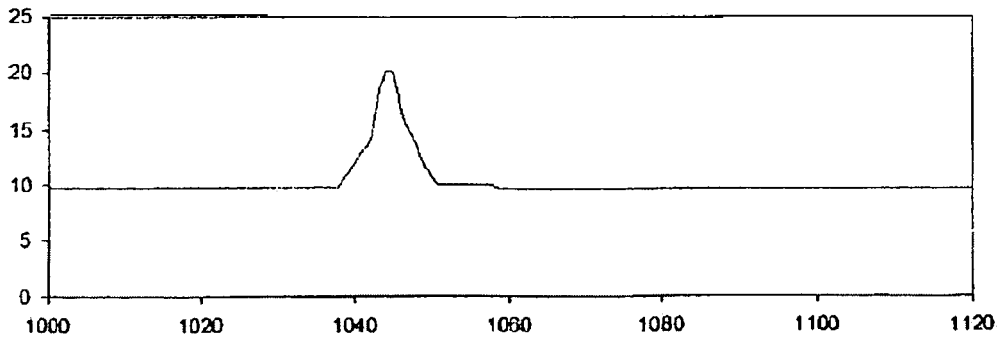
FIG. 19 is a graphical representation of a deletion according to the present invention.

Insertion and deletion are additional or missing bases in a DNA sequence, as compared to what is considered a normal DNA sequence. Insertion and deletion can be determined using the alignment process discussed in the above method to find mutations in a DNA sequence. Whereby, the data of the sample sequence trace data is compared to the aligned sequence trace data produced from alignment of reference and sample trace data. FIG. 16 shows an example of reference sequence trace data which is used with a sample sequence trace data shown in FIG. 17. FIG. 18 shows the aligned sequence trace data of FIG. 17. The data of the sample sequence of FIG. 17 is compared to the data of the aligned sequence of FIG. 18, to determine if there are any insertions or deletions. First, using the trace data from the sample sequence trace data of FIG. 17, pairs of data points are chosen on a frame number scale from any of the trace data for different positions among the trace data set for the sample sequence. An example of one chosen pair is A on the electropherogram of FIG. 17, which is about average spacing of a base. Usually, the scale is 10 frame numbers between each pair of data points. Second, the pairs of chosen data points are located within the trace data set of the aligned sample sequence trace data. FIG. 18 shows B as an example of the same chosen pair A located on the electropherogram of the aligned sequence trace data. The frame numbers are measured between each of the located pairs and plotted as shown in FIG. 19. A dramatic increase or decrease in the frame number spacing between data points will be plotted as a well defined peak and indicates an deletion or insertion, respectably. FIG. 19 shows a plot peak of dramatic increase to indicate a deletion. The process of finding insertions or deletions can also be applied using the reference sequence from which to chose the pairs of points to be located within the trace data set of the aligned sample sequence trace data. When using the reference sequence, a dramatic increase or decrease in the frame number spacing between data points will indicate a insertion or deletion, respectably.

Figure 20:
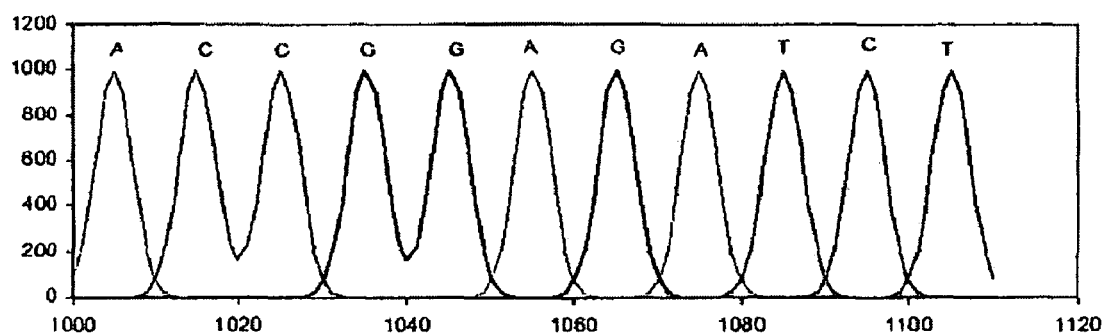
FIG. 20 is a reference DNA sequence electropherogram according to the present invention. (seq. ID No. 12)
Figure 21:
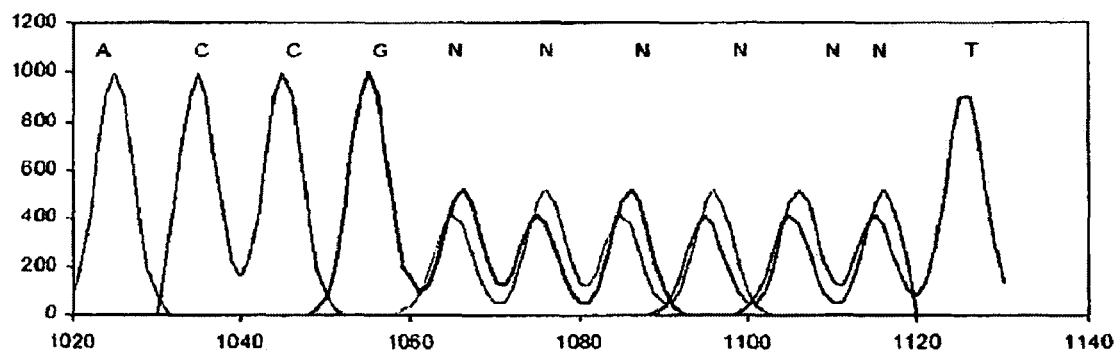
FIG. 21 is a sample DNA sequence electropherogram according to the present invention. (seq. ID No. 13)
Figure 22:
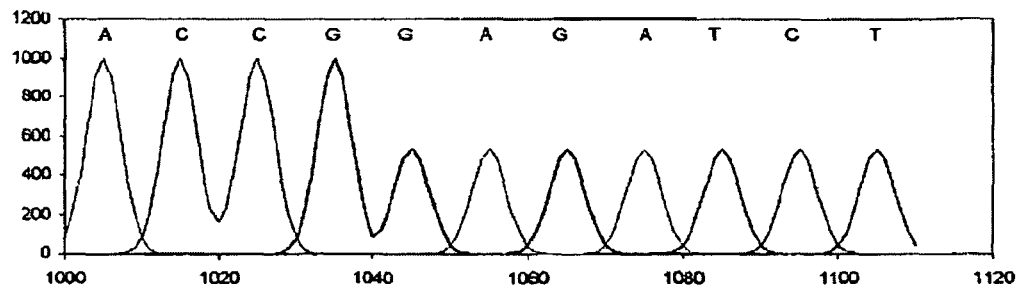
FIG. 22 is an adjusted reference DNA sequence electropherogram according to the present invention. (seq. ID No. 14)
Figure 23:
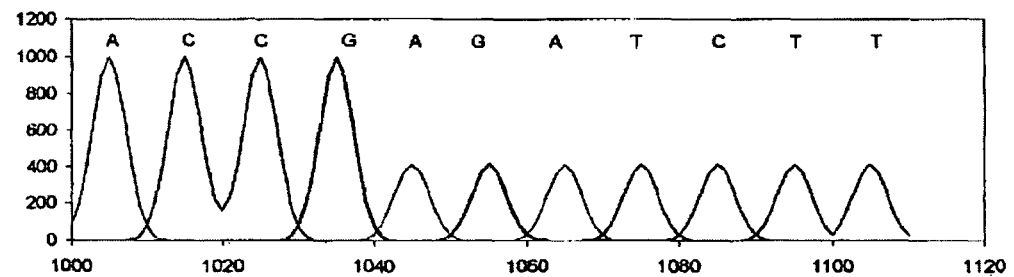
FIG. 23 is an adjusted sample DNA sequence electropherogram according to the present invention. (seq. ID No. 15)
Figure 24:
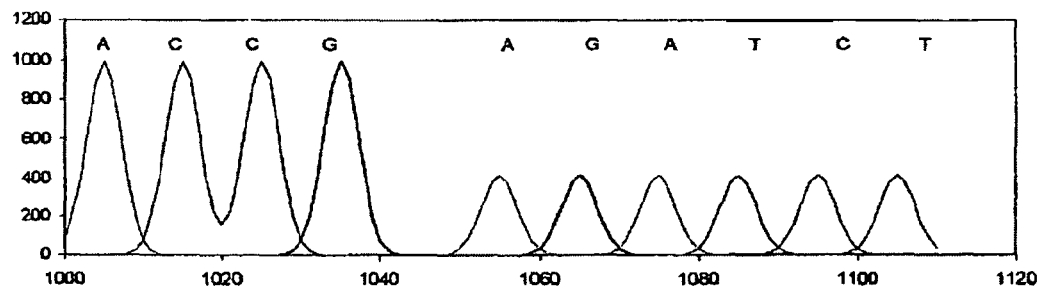
FIG. 24 is an aligned sample DNA sequence electropherogram according to the present invention. (seq. ID No. 16)

A specific type of insertion and deletion which proves more difficult to analyze is heterozygous insertions and deletions. Heterozygous DNA sequence is a more complicated of DNA. The electropherograms of heterozygous insertion and deletion are difficult to use in order to distinguish bases, due to the complexly of the plotted traces, which are shown in FIG. 21. This because the electropherogram of a heterozygous DNA sequence shows a mixture of two components of the DNA, making it hard to distinguish between peaks. For this example, FIGS. 20-24 show a theoretical depiction of a heterozygous deletion. FIG. 20 is the reference DNA sequence utilized to determine if there is any insertion or deletion. In the case of heterozygous insertions and deletions, the same basic procedures are utilized, such as alignment and intensity normalization. What must be further done is to simplify the data so it can be easily interpreted by a user. A means to simplify the data is to use a subset of the reference traces to subtract a portion of sample traces during alignment. An intensity ration is used for the subtraction process. The intensity ratio is peak intensity value of the sample of a base divided by the peak intensity value of the same base in the reference sequence. The intensity ratio starts from the data with multiple N basecalling. N means undetermined basecalling where multiple peaks are shown at the same frame number for a base. The ratio is determined by the computer to search for the peak intensity when the peak is under a major peak. The computer subtracts the adjusted reference data from the data shown in FIG. 21 to produce an adjusted sample trace data as shown in FIG. 23. FIG. 22 shows the data remove from FIG. 21 and represents the reference portion in the sample sequence. Then, the data in FIG. 23 is aligned with the data in FIG. 20 to produced the align trace data of FIG. 24. This is only done to the right side of the data of FIG. 21. The left side of electropherogram of FIG. 21 shows the identical bases ACCG in both the reference and sample sequences of FIGS. 20 and 21. There is no need to adjust the data on the left side of FIG. 21. Finally, the data in FIG. 24 is related to the data of FIG. 21, as discussed above for finding insertion or deletion. The computer iterates the subtraction process until the reference portion in the sample trace reaches minimum.

Figure 25:
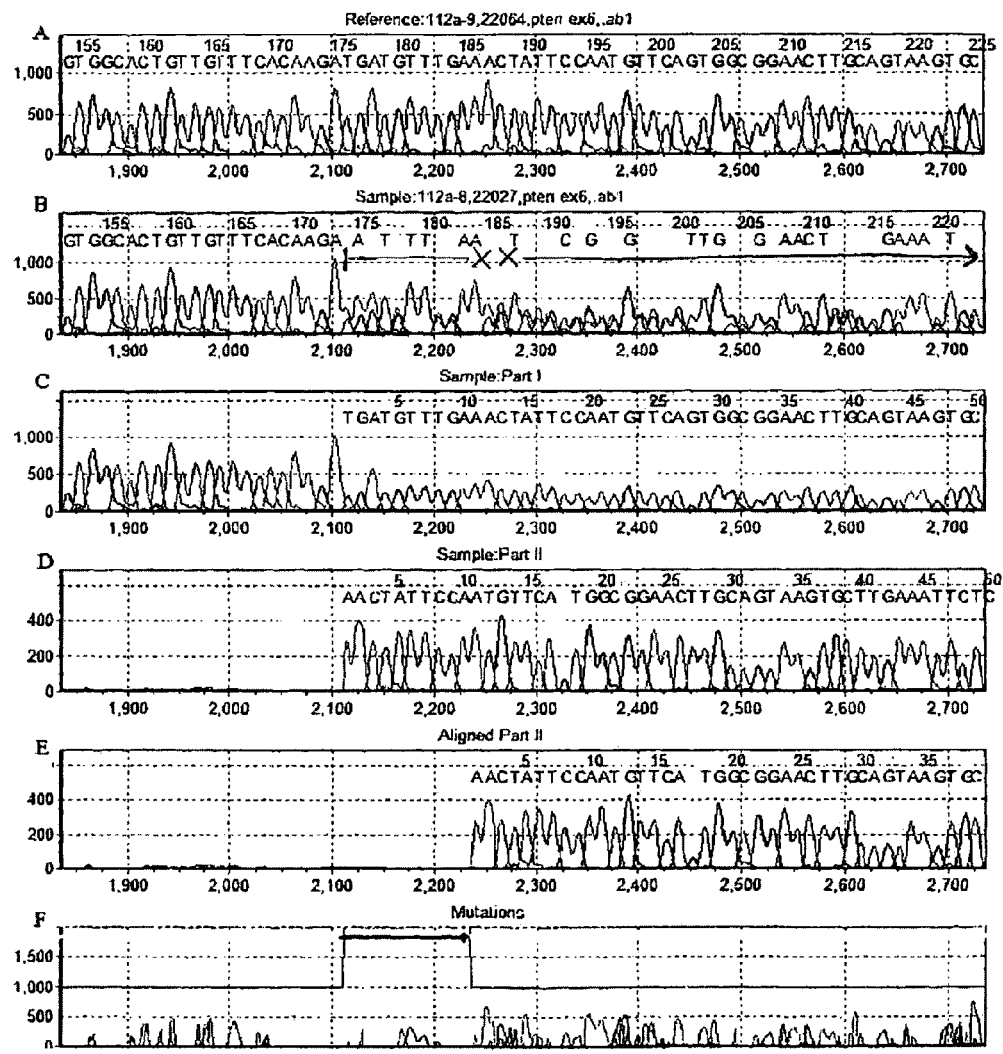
FIG. 25 is a series of electropherograms to depict a insertion and deletion according to the present invention. (seq. ID No. 17-21)

The following is a real life example of finding heterozygous insertion or deletion. In the same contig, we have a reference and a sample. The reference sequence traces are shown in FIG. 25 as plot A and the sample sequence trace is shown in FIG. 25 as plot B which is a example of heterozygous deletion. It is assumed for this example that it is not known that FIG. 25 as plot B is a mutation sample of heterozygous deletion To find a heterozygous insertion or deletion, the subtraction method is used to break a DNA sequence trace into two sets of sequences and isolate a few bases in one of the sets of sequences which include the insertion or deletion. Then, the measured sequence is shown as a mixture of two sequences after the heterozygous insertion or deletion point. FIG. 25 as plot B shows such an example of the sample from which the process is started. The first step is to align the mutant sample to reference. As shown in plot B of FIG. 25, the side of the plot to the left of section XX is not as complicated and can be easily aligned with the reference plot A without using any subtraction process. In which the previous discussed methods of global and accurate alignments are used to align the left side of plot B to plot A. At the right side of electropherogram, the global alignment becomes complicated due to the trace data in section XX shown in plot B. Therefore, the subtraction process must be used to adjust the data of the right side of plot B to improve alignment of the sample and reference trace data of FIG. 25.

Next, the accurate alignment of the right side of the electropherogram of plot B is performed. First it is found that there are some peaks in the right side of the sample which appear as a clean base and have intensities for these peaks are higher than that of the mixture peaks. These peaks are unaffected peaks. For an unaffected peak, it must be a peak of the same color as compared to a peak of the reference at a particular frame number. A color of the trace is chosen in the sample that has least of number of peaks. The least number of the peaks is used to align with the reference trace of the same color, because it is the least complicated. For example, the G trace of mutant sample is used to compare to the reference G trace. Frequently, there might be one or two alignment possibilities. Then, the other color traces are used to confirm the alignments and to eliminate the illogical alignment, starting with the trace with second least number of peaks. The use of the other color traces to confirm alignment involves the following. All of the traces will also have at least two possible positions for the a peak. By considering what should be the peak for the first trace, the traces of the other peaks will be positioned along a logical value for the frame number for the other peaks. If there is no logical arrangement of the other peaks, the first peak choice is wrong. If there is a logical arrangement, then the first peak choice is correct. Since we have four traces corresponding for four bases, we will get to the right answer after confirming with other three traces. After the alignment, the intensities of the reference are subtracted with a ratio from intensities of mutant. The ratio is determined from the intensity ratio of the unaffected peaks between mutant sample and reference times 0.6, which is assumed that the ideal mutant consists about 0.5 of reference intensity. The software will iterate the subtraction process until all of its components from reference are subtracted. Note that there is no subtraction of the left side of the electropherogram. After the subtraction process, the results are the traces of the mutant after deletion, as shown by plot D in FIG. 25, since most the components similar to the reference are subtracted out. The left side of the sample DNA sequence is not shown for clarity. Then, the adjusted traces in plot D are used to subtract from the raw data in plot B. The traces of the mutant which are similar to reference are shown as plot C in FIG. 25. After these iteration steps, the mixture on the right sides has been completely deconvoluted of the mixture of the two DNA components. Then, the traces of shifted mutant component are aligned with the reference, as shown in plot E of FIG. 25. The heterozygous insertion and deletion is then determined after the alignment in the same manner of regular insertion and deletion. The example in plot F of FIG. 25 shows a heterozygous deletion of ten nucleotides, TGATGTTTGA (seq. ID No. 3). The process described above for heterozygous insertion and deletion is completely incorporated into computer software. Also, the subtraction process is one means to accurately align a heterozygous insertion and deletion. Other means can by employed, such as a mathematical function in an anti-correlation calculation scheme using the reference and sample DNA sequences.

As discussed before, a scoring system can be utilize to give the user confidence in the results of the above method. To create the scoring system, it was determined that certain factors of overlapping factor, intensity dropping factor and deflection factor are used. Overlapping factor as discussed above eliminates many false positive peaks due to the peak overlapping. The intensity dropping factor represents the intensity dropping ratio. The homozygous and heterozygous mutation is often associated with a intensity dropping. Intensity dropping factor is defined as the relative intensity drop, when the sample peak is compared to the reference traces in the local region.

Figure 26:
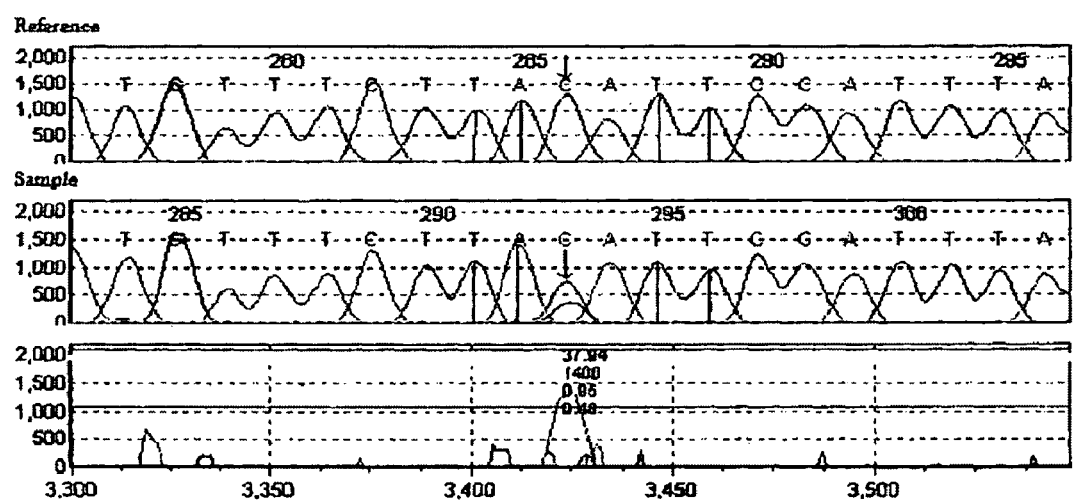
FIG. 26 is a series of electropherograms to depict a dropping factor according to the present invention. (seq. ID No. 22-23)

As shown in FIG. 26, four neighboring peaks are used, two from right side and two from left side, to compare to the mutation peak. The closest right peak is not used for the calculation because its intensity changes with the mutation. The dropping factor is defined as $$\text{dropping\_factor} = 1 - \frac{4\frac{I_{s,mut,x}}{I_{r,mut,x}}}{\frac{I_{s,left1,u}}{I_{r,left1,u}} + \frac{I_{s,left2,v}}{I_{r,left2,v}} + \frac{I_{s,right1,w}}{I_{r,right1,w}} + \frac{I_{s,right2,y}}{I_{r,right2,y}}}$$

The three subscripts indicate the sample/reference (s/r), positions such as mutation position (mut) or left1 or right 2, and types of nucleotides. The above example shows x=C, u=T, v=A, w=T, and y=T. The intensity of C of sample in this figure is dropped 48% compared to the reference. Ideally, the intensity dropping factor is 1.00 when it is homozygous mutation, and 0.50 for heterozygous mutation.

Deflection factor, $\mu_{df}$, is defined as the sample data at a mutation peak as it is changing from curve up to curve down, representing a peak. A deflection around mutation peak will definitely indicate a mutation. The overlapping peak will have zero score in deflection, because there is not any deflection point in the curve.

In a mutation electropherogram, there are 12 colors of the mutation electropherogram traces representing AC, AG, AT, CA, CG, CT, GA, GC, GT, TA, TC, and TG. The mutation intensity changes significantly in the mutation electropherogram if there is a mutation. Since the mutation occurring rate is about 1/1300 in the human genome, and the rate of smaller peaks being a mutation in a 10-base region after excluding a big peak is 1/130. In fact, the first three strongest peaks are excluded in the mutation electropherogram of a 10-base local region, and the rate of fourth peak being a mutation is $(1/130)^3 = 0.45 \times 10^{-6}$. The fourth peak intensity is taken as noise intensity. The first three mutation peak intensities are taken as signal intensities.

The following is a system of equations to provide a scoring value.
Probability of Gausian Distribution (−∞, +∞).

$$y = \frac{1}{\sqrt{2\pi}\,\sigma} \exp\left[-\frac{(x)^2}{2\sigma^2}\right]$$

Where σ is distribution width being a noise in our case. x/σ is signal to noise ratio. In our case, x>0, therefore the probability of the data in the range of (0, x) is $$y = \int_0^x \frac{2}{\sqrt{2\pi}\,\sigma} \exp\left[-\frac{(x)^2}{2\sigma^2}\right] dx$$

Let x/sqrt(2)σ=u, then $$y = \int_0^x \frac{2}{\sqrt{2\pi}\,\sigma} \exp\left[-\frac{(x)^2}{2\sigma^2}\right] dx = \int_0^{s/n\sqrt{2}} \frac{2}{\sqrt{\pi}} \exp[-u^2] du = erf\left(\frac{s/n}{\sqrt{2}}\right)$$

complementary error function erfc(x)=1−erf(x)
When s/n=1; y=68%; error 32%
S/n=2; y=95.5%; error 4.5%
S/n=3; y=99.7%; error 0.3%
Mutation Score=−10 log (error)

$$\text{Therefore mutation score} = -10\log\left[erfc\left(\frac{s/n}{\sqrt{2}}\right)\right]$$

There are three parameters to be used. The three parameters are overlapping factor, intensity dropping factor, and signal to noise ratios (s/n). To provide a score value for a mutation, three parameters are fuse by the following formula.

Mutation score =

$$-10\log\left[erfc\left(\frac{s/n}{\sqrt{2}}\right)*\text{dropping\_factor}*\text{overlapping\_factor}\right]$$

Alternatively, we may develop another score system. There are many possible score systems. The following is a another example. Since there are basically two types of mutations, type one, homozygous and heterozygous point mutations, and type two, insertion and deletion, two scoring systems for mutation detection must be provided. Type one mutation is based on the anti-correlation electropherogram to detect possible homozygous and heterozygous point mutations. Type two mutation, deletion and insertion, is based on the space continuation after alignment referenced to the wide-type sequence. There are many parameters associated with a potential mutation peak. All of the parameters should be judged with a combined score for each type of mutation.

For type one mutation, the present invention uses five parameters in mutation electropherogram, peak height $H_p$, peak area $A_p$, overlapping factor $f_o$, intensity dropping factor, $f_{id}$, and deflection factor, $f_{df}$. Peak area is not an independent parameter, since it is closely relative to peak height. The scoring of type one mutation is defined as $$\text{Score\_1} = \log(H_p/1000) + 2f_o^2 + 2f_{id}^2 + 2f_{df}^2$$

It is found that above formula can well represent with data of mutation type 1. The threshold of the score will be 4 to call it as potential mutation.

For type two mutation, insertion and deletion, one distant parameter will be enough. The distant parameter is defined as $$f_{space} = (S_{mut} - S_{avr})^2 / S_{avr}^2$$

where $S_{mut}$ is the distant of mutation peak, and $S_{avr}$ is the average distant. It is normal to take 10 frames before alignment, and then calculate how much the 10 frames will be changed to after alignment to determine if there is an insertion or deletion. Based on the scoring system, it is easy to identify the mutation peaks. All of above system will subject intensive test.

Another step which can be added to the method to check if the mutation calculations are reasonable is to perform two direction mutation calculation. Two direction mutation calculation involves the step of performing the above method from both strands of the DNA sample sequence. First, the mutation calculation is performed in the normal direction from left to right along one of the strands of the DNA sample sequence. Then, the mutation calculation is performed in the opposite direction of right to left of the other strand of the DNA sample sequence. But, there are two additional steps are needed to compare the sample to the reference when proceeding in the opposite direction. The first step is to reverse the order of the sequence letters of the sample. For example, if reading right to left the sequence is CATGA, then it is reversed to AGTAC. The second step to change the lettering of the reversed sequence to match with the reference, since the reference is always read left to right. To do this, the bases of the reversed sequence are change to their complementary base letters, where G and C complement each other and T and A complement each other. Therefore, the reversed example of AGTAC would be changed to GTACT. This sequence of GTACT then aligned with the reference sequence and the method of the present invention is performed.

The anti-correlation calculation of the above method solves a big problem that none of the prior art has solved. The problem is that the sequence data from two different dye chemistries show different peak intensity, such as BigDye version 2 and BigDye version 3. The relative intensity variations are significant when comparing two different dye sets, for example, ABI BigDye and Amshan ET dyes. The relative intensity variation from two instruments such as ABI Prism 3700 and MegaBase 1000 are significantly high. The method using software can take any data sets from any dye sets and from any instruments to find mutations. Additionally, a method of relative peak intensity drop can be used for detecting DNA variation in a sample DNA sequence and can be used for comparing the results of the anti-correlation calculation scheme discussed above. By comparing the intensity of base peak trace data of a reference DNA sequence relative to intensity of base peak trace data of a sample DNA sequence, a DNA variation can be found. This is done by ignoring all base peak trace data of the sample DNA sequence which does not show a drop in intensity as compared to the same trace data of the same base peak of the reference DNA sequence. Then, any base peak trace data of the sample DNA sequence which is not ignored indicates a variation in the sample DNA sequence. The alignment is not needed to detect mutation with the relative intensity drop process. Intensity normalization is not required to calculate the relative intensity drop.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof

We claim:

1. A method for detecting insertion and deletion in a sample DNA sequence, comprising:

using a computer to align trace data of a sample DNA sequence that is aligned to trace data of a reference DNA sequence to produce an aligned sample DNA sequence, whereby the trace data of the reference DNA sequence and the trace data of the sample DNA sequence include frame numbers;

using a computer to chose pairs of data points from any of the trace data for different positions along the trace data of the reference DNA sequence or the sample DNA sequence before alignment, whereby the number of frame numbers between the chosen pairs is the same for each chosen pair;

using a computer to locate the chosen pairs of data points chosen from either the reference DNA sequence or the sample DNA sequence in the aligned sample DNA sequence;

using a computer to measure the number of frame numbers between the located chosen pairs of data points in the aligned sample DNA sequence; and finding any increase and decrease of number of frame numbers from the measured number of frame numbers of the aligned sample sequence as compared to the same number of frame numbers used when choosing the paired data points from either the reference DNA sequence or the sample DNA sequence before alignment, whereby a dramatic increase is an insertion and a dramatic decrease is a deletion if the chosen points are from the reference DNA sequence and whereby a dramatic increase is a deletion and a dramatic decrease is an insertion if the chosen points are from the sample DNA sequence before alignment.

2. The method of claim 1, wherein the same number of frame numbers used when choosing the paired data points of the sample sequence before alignment is ten frame numbers.

3. The method of claim 1, wherein the difference between the measured number of frame numbers of the aligned sample sequence and the same number of frame numbers used when choosing the paired data points of the sample sequence before alignment is plotted to show any dramatic increase and decrease in the frame number after alignment to indicate a deletion and insertion.

4. The method of claim 1, wherein during aligning of the reference DNA sequence trace data to the sample DNA sequence trace data, a general alignment is performed by finding identical bases contained in the reference and sample DNA sequences and then the sample DNA sequence trace data is adjusted to match the sample DNA sequence trace data to the reference DNA sequence trace data.

5. The method of claim 4, wherein an additional alignment is performed after the general alignment has been performed to provide an increase in accuracy.

6. The method of claim 1, wherein said sample DNA sequence qualifies as a heterozygous insertion and deletion; and wherein using a correction process during alignment of the reference and sample DNA sequences in areas of the sample DNA sequence which are cluttered with data, to align in order to remove trace data of the sample DNA sequence which is not required for alignment.

7. The method of claim 6, said correction process is a subtraction method between the reference and sample DNA sequences.

8. The method of claim 6, wherein an intensity ratio is used for the subtraction process; wherein the intensity ratio is peak intensity value of a base of the sample DNA sequence divided by the peak intensity value of the same base in the reference DNA sequence; and wherein subtraction using the intensity ratio is used where multiple peaks are shown at the same frame number in the sample DNA sequence.

9. The method of claim 6, wherein said correction process is a mathematical function in an anti-correlation calculation scheme using the reference and sample DNA sequences.

10. The method of claim 6, further including normalizing the trace data of the reference DNA sequence and the trace data of the sample DNA sequence after alignment of the trace data of the reference DNA sequence and the trace data of the sample DNA sequence to create normalized trace data for the reference DNA sequence and the sample DNA sequence.

11. The method of claim 6, wherein during aligning of the reference DNA sequence trace data to the sample DNA sequence trace data, a general alignment is performed by finding identical bases contained in the reference and sample DNA sequences and then the sample DNA sequence trace data is adjusted to match the sample DNA sequence trace data to the reference DNA sequence trace data.

12. The method of claim 11, wherein an additional alignment is performed after the general alignment has been performed to provide an increase in accuracy.

* * * * *